United States Patent [19]

Curtain et al.

[11] Patent Number: 4,554,390
[45] Date of Patent: Nov. 19, 1985

[54] METHOD FOR HARVESTING ALGAE

[75] Inventors: Cyril C. Curtain, Williamstown; Harvey Snook, Aspendale, both of Australia

[73] Assignees: Commonwealth Scientific and Industrial Research Organization; Betatene Limited, both of Australia

[21] Appl. No.: 511,135

[22] PCT Filed: Oct. 7, 1982

[86] PCT No.: PCT/AU82/00165

§ 371 Date: Jun. 7, 1983

§ 102(e) Date: Jun. 7, 1983

[87] PCT Pub. No.: WO83/01257

PCT Pub. Date: Apr. 14, 1983

[30] Foreign Application Priority Data

Oct. 7, 1981 [AU] Australia ............................... PF1093

[51] Int. Cl.[4] .......................... C07C 29/76; C12N 1/02; A01D 44/00; B01D 15/08

[52] U.S. Cl. ....................................... 568/870; 47/1.4; 426/429; 426/431; 568/869; 585/809; 585/811; 585/829

[58] Field of Search .................... 47/1.4; 505/809, 811, 505/829; 568/870, 869; 426/429, 431

[56] References Cited

U.S. PATENT DOCUMENTS

| | | | |
|---|---|---|---|
| 2,620,334 | 12/1952 | Nielsen et al. | 426/431 |
| 4,112,223 | 9/1978 | Lin et al. | 426/431 |
| 4,115,949 | 9/1978 | Arron et al. | 47/1.4 |
| 4,199,895 | 4/1980 | Arron et al. | 47/1.4 |
| 4,320,050 | 3/1982 | Rebeller et al. | 426/431 |
| 4,341,038 | 7/1982 | Bloch et al. | 47/1.4 |

FOREIGN PATENT DOCUMENTS 486999 2/1976 Australia .

OTHER PUBLICATIONS

The Merck Index, Ninth Edition, (1976), p. 237.

Primary Examiner—J. E. Evans
Attorney, Agent, or Firm—Sughrue, Mion, Zinn, Macpeak, and Seas

[57] ABSTRACT

A method for harvesting algae of the genus Dunaliella from suspensions thereof in brines containing sodium chloride at a concentration of about 3M or above, wherein the algal suspension is contacted with an adsorbent having a hydrophobic surface so as to adsorb the algae thereon, and the adsorbent with the algae adsorbed thereon is separated from the brine.

$\beta$-carotene and other useful cell components may be extracted from the adsorbed algae by treatment with a suitable solvent.

19 Claims, No Drawings

METHOD FOR HARVESTING ALGAE

This invention relates to a method for harvesting algae from salt solutions and especially to the harvesting of halotolerant unicellular algae belonging to the genus Dunaliella. The invention also relates to the recovery of carotenes, especially β-carotene, chemically related carotenoids, triterpenes, glycerol and proteinaceous material from the harvested algae.

Algae which contain carotenes, carotenoids and triterpenes commonly occur as a natural growth in saline lakes and lagoons. Such algae may also occur naturally and/or may be cultivated in saline ponds, such as those used in conjunction with solar evaporation complexes, which may also include means for varying the content of carbon dioxide in the water in order to control or enhance growth of the algae. The saline material or salt solutions containing the algae are commonly referred to as "brine".

The carotenes, carotenoids and triterpenes in the algae may be recovered from same in the form of a liquid or as pure and crystalline materials defined as "carotene". This is a mixture comprising mainly β-carotene and its isomers and similar substances. Carotene is of value as a source of pro-vitamin A, which is converted in the human body to vitamin A, and as a natural food colouring agent for use, for example, in the colouring of margarine, soft drinks and other edible products.

The investigations of carotene-rich algae upon which this specification is based have been particularly directed to the species *Dunaliella salina*. It is to be understood, however, that the invention is also applicable to other algae which may have an economically recoverable carotene content.

Algae may be recovered from brine by various flotation processes. These processes all include steps in which the algal cells are subject to disintegration. This disintegration is found necessary to float the algal material to the surface of the brine. However, the need for disintegration of the algal cells and for the introduction of finely dispersed air bubbles to assist flotation of the algal material places relatively high energy requirements on the process and also leads to oxidation of the caroteniferous materials in the algal cells. (The term "caroteniferous materials" is used herein to cover both carotenes and carotenoids.) It has also been found that by using the flotation process outlined, the recovery of only approximately 70% of the algae present in the brines is obtained.

Algae of the genus Dunaliella are known to contain β-carotene and to consist of motile single cells 10–20 μm in diameter and having a specific gravity of about 1.1. As a consequence of their low specific gravity the cells do not readily sediment, especially from brines whose specific gravity is greater than unity. The algae can contain up to 50 percent of their dry weight of glycerol and up to 10 percent of their dry weight of β-carotene when grown in sodium chloride solution of 3M concentration. They occur naturally at concentrations of about 50 mg/litre in the brine pools of salt fields but concentrations of about 300 mg/litre can be attained when the algae are grown in specially constructed ponds.

The prior art has been mainly directed towards the growth of the organisms and to the use of centrifugal and filtration methods to separate and concentrate the organisms from the nutrient brine in which they have been grown. In U.S. Pat. Nos. 4,115,949 (corresponding to Australian Patent Application No. 25,773/77) and 4,199,895 Avron and Ben-Amotz disclose a process for the simultaneous production of glycerol, β-carotene and a protein-rich material of nutritive value from algae of the genus Dunaliella. The algae are grown under controlled conditions in a nutrient medium, initially at a sodium chloride concentration of at least 1.5M and later at a sodium chloride concentration of at least 3M. The algae are harvested by a variety of means such as sedimentation, flocculation, filtration or centrifugation. Further centrifugation is then used to concentrate the algae prior to the extraction of glycerol and the carotene with organic solvents. However, centrifugation is an inherently costly method of separation on account of the high capital and operating costs of centrifuges which are exacerbated by the corrosive nature of salt solutions. Centrifuging is therefore not an economical method of harvesting algae from saline media. The use of flocculants is likewise unsatisfactory as the algal flocs occlude large volumes of the saline solution and sediment only slowly.

Australian Pat. No. 486,999 discloses a filtration process for the recovery of caroteniferous algae from brine suspensions thereof in which a filter aid is added to the algal suspension prior to recovery of the filter aid and the algae by filtration. The disadvantages of this process include the tendency of the microscopic algae to block the filter, thus reducing the flow rate, and the admixture of the desired algae with a large volume of filter aid from which the algae are not readily separable.

A further disadvantage of the aforesaid prior art processes for harvesting algae from brines is that the halobacteria frequently present in such brines are also harvested in admixture with the desired algae. When such a mixture of halobacteria and algae is extracted with solvents to recover its carotene content, the carotene obtained is found to be impure and contaminated with undesirable carotenoids and lipids derived from the halobacteria.

We have discovered that the cell membrane of algae of the genus Dunaliella becomes hydrophobic when the algae are in contact with solutions of sodium chloride having a concentration of about 3M or higher, and that this behaviour enables the algae to be adsorbed on to substances having a hydrophobic surface, thus providing a means whereby the algae can be rapidly and economically separated and recovered from the saline medium in which they have been grown. We have also found that at lower concentrations of sodium chloride such as that found in sea water the surface of the cell membrane is dominated by polar groups and is not hydrophobic and hence the algae will not adsorb or remain adsorbed on a hydrophobic surface.

Thus we provide a method for harvesting algae of the genus Dunaliella from a suspension thereof in a brine containing sodium chloride at a concentration of about 3M or above, which method comprises contacting the algal suspension with a hydrophobic adsorbent so as to adsorb the algae thereon, and separating the adsorbent with the algae adsorbed thereon from the brine.

The method of the invention may further include treating the thus separated adsorbent with water or a brine of lower salinity so as to release the adsorbed algae In a preferred aspect the invention also includes a method for recovery of the cell contents of the algae while still attached to the separated adsorbent, which method comprises contacting the algae with a suitable solvent so as to disrupt the cell membrane of the algae and release the cell contents for recovery by solvent extraction or other known means.

Preferably the solvent selected is also a solvent for β-carotene and thus performs the dual functions of cell disruption and β-carotene extraction.

The method is also applicable to harvesting the algae from brines in which the sodium chloride concentration is below that at which adsorption on to hydrophobic substrates occurs. In this case the brine concentration can be adjusted upwards to the appropriate level.

It should be noted here that the change from hydrophilic to hydrophobic behaviour of the algae is not abrupt, i.e., it does not occur at a specific concentration. The transition, however, does take place when the concentration is about 3M.

Suitable hydrophobic adsorbents for the practice of the invention include organic polymers such as poly-(alkylenes), e.g. polyethylene or polypropylene, polyamides, e.g. Nylon, polyesters, polyacrylates, polyacrylonitriles and fluorinated polymers, e.g. Teflon. The polymers are preferably in the form of finely divided powders or fibres having a high surface area. Other adsorbents having a high surface area may be used provided they are hydrophobic or have been rendered hydrophobic by suitable means as, for example, by treatment with a suitable silane or silicone. Silanized glass wool or beads are particularly useful as hydrophobic adsorbents for the practice of the invention. Finely divided hydrophobic minerals may also be used. Satisfactory minerals include the sulphide mineral chalcopyrite and the oxide minerals rutile, haematite, ilmenite, magnetite and pyrolusite. Magnetite in particular has been found to be a good adsorbent for the algae and has the advantage that it can be readily separated and recovered from the saline solution by magnetic means. Hydrophobic organic materials such as finely powdered graphite and anthracite have also been found to be good adsorbents for use in the practice of the invention.

There are several ways in which the method can be applied to the harvesting of Dunaliella species from concentrated brines, one such way being the technique known as hydrophobic filtration in which a suspension of the algae in a suitably concentrated (3M) brine is passed through a loosely packed bed of hydrophobic material such as silanized glass wool. The algae are readily retained on the surface of the glass wool and may be subsequently eluted by passing a more dilute brine, such as 0.5M sodium chloride, through the bed. This technique may be adapted to either column filtration or to a moving belt filter in which the belt is constructed of suitable hydrophobic material. Another separation technique based on the same principle involves introducing a fine dispersion of a hydrophobic adsorbent of density less than unity into the algal culture and allowing the algae to adsorb thereon, whereupon the algae may then be harvested by flotation. Yet another approach is to adsorb the algae on to hydrophobically coated magnetite particles such as those which have been used for the separation of oil from water.

A feature of the invention is that the spent adsorbent can be reactivated for further use by washing it with water or with sodium chloride solutions of concentration less than 1 molar.

Use of the method for the recovery of Dunaliella species from a suspension thereof in brine was demonstrated using brine from a natural saline lake in Victoria. The brine was essentially saturated with respect to sodium chloride and was typical of brines from such sources in being contaminated with clay, halophilic bacteria and other extraneous materials. Examination of the sample showed that the number of cells per unit volume was higher than is typically found in such natural saline waters and that the cells were mainly viable. Only a few lysed cells and fragments of free lipid and free β-carotene were present. The individual intact cells contained a high concentration of β-carotene relative to the concentration of chlorophyll therein.

The cell suspension was passed through porous adsorbent plugs comprised of hydrophobic fibres made from nylon 66, polyester, a polyacrylate, Teflon (polytetrafluoroethylene) and glass wool which had been rendered hydrophobic by treatment with a suitable silane. In each case good adsorption of the Dunaliella cells was found to occur and the adsorbed algal cells were retained during subsequent rinsing of the plugs with cell-free saturated sodium chloride solution to remove occluded clay, bacterial cells and other extraneous materials which had been present in the original suspension. A solution of sodium chloride of concentration less than 1 molar was then allowed to percolate through the plugs on which the algal cells had been adsorbed, whereupon it was observed that the cells were readily desorbed from the adsorbent and passed out of the system with the effluent liquor. The thus regenerated adsorbent plugs were found to be capable of adsorbing more Dunaliella cells from a fresh sample of the saline brine and the cycle repeated many times.

The adsorption of Dunaliella cells on to a hydrophobic adsorbent in the manner described allows the cells to be concentrated and facilitates the recovery of their β-carotene content. We have found that Dunaliella cells while still adsorbed on the hydrophobic adsorbent can be disrupted by a solvent capable of damaging the cell membrane and that a suitable choice of solvent will allow the β-carotene to be extracted leaving the cell debris and insoluble cell components still adsorbed on the hydrophobic surface.

Solvents suitable for this purpose include but are not limited to chlorinated solvents such as methylene dichloride, chloroform, carbon tetrachloride and trichlorethylene, and aromatic hydrocarbons or mixtures of aromatic and aliphatic hydrocarbons. Hydrocarbons such as benzene, toluene and commercial petroleum fractions containing mixtures of aromatic or aliphatic and aromatic hydrocarbons are suitable. Aromatic hydrocarbons are more suitable than aliphatic hydrocarbons as they possess greater dissolving power for caroteniferous materials. To assist the subsequent recovery of the β-carotene, solvents of relatively low boiling point of about 100° C. or less are preferred. Liquid carbon dioxide is also a suitable solvent for the extraction of β-carotene and its low boiling point minimizes the tendency for decomposition of the extracted caroteniferous materials during their separation and isolation.

The soluble component also contains triterpenoids and lipids as well as β-carotene. These components can be easily separated from the β-carotene, e.g., by fractional crystallisation and/or solvent partitioning, and can be recovered for other uses, for example, as chemical raw materials.

The cell debris left after extraction of the β-carotene may be desorbed from the adsorbent by washing the latter with dilute sodium chloride solution or water in the manner hitherto described and the thus regenerated adsorbent may be recycled for further use.

The cell debris, which is a proteinaceous material, may be recovered by any suitable means and used, for example, as a stock food or protein supplement, or as a protein source for other applications.

The water-soluble cell contents, principally glycerol, may also be recovered from the wash liquor.

The principles and practice of the invention are further illustrated by the following examples. These examples are not to be construed as limiting the invention in any way.

EXAMPLE 1

Glass wool was "silanized" and rendered hydrophobic by immersion for 10 minutes in a 10% v/v solution of dichlorodimethylsilane (Union Carbide silane A156) in hexane. The treated glass wool was then washed five times with distilled water. A column 15 cm in length and 7 cm outside diameter was carefully packed with 90 g of the thus treated glass wool and 1.5 litres of a suspension of *Dunaliella salina* cells in saturated sodium chloride solution and containing $10^5$ cells/ml was passed through the column at a flow rate of 1.3 l/min. The column was then drained and 700 ml of methylene dichloride passed therethrough. The effluent methylene dichloride was collected and analysed to determine its content of β-carotene, which was established to be 77% of the β-carotene present in the cells contained in the original solution.

The glass wool was then reactivated by passing 1.6 litres of distilled water through the column to desorb and flush out residual cell debris. The reactivated glass wool was reused in an identical experiment with a further sample of the same Dunaliella suspension and substantially identical results were obtained.

EXAMPLE 2

Magnetite (10 g, passing a 20 mesh (BSS) screen) was silanized with a 10% v/v solution of dichlorodimethylsilane in hexane for 20 minutes, then washed with water and dried at 110° C. The silanized magnetite was stirred with 50 ml of a suspension of $2 \times 10^5$ cells/ml of *Dunaliella salina* in a saturated sodium chloride solution for 10 minutes. The silanized magnetite was then removed from the solution by using a permanent magnet. The cells adsorbed on the magnetite were lysed by contacting the magnetite with methylene dichloride, after which the methylene dichloride was separated and analysed to determine its content of β-carotene. It was found that 87% of the β-carotene present in the original suspension of Dunaliella cells had been recovered in the methylene dichloride.

The silanized magnetite was reactivated by washing five times with 10 ml portions of water. The experiment was then repeated using the reactivated magnetite and 70% of the β-carotene present in the Dunaliella cell suspension used was recovered in the methylene dichloride.

EXAMPLE 3

Polyester fibre (1 g) was carefully packed into a column 20 cm in length and 1.5 cm outside diameter. A suspension of *Dunaliella salina* cells ($2 \times 10^5$ cells/ml) in saturated sodium chloride solution was passed through the column at the rate of 8 ml/min. The fibre was then washed with 20 ml of saturated sodium chloride solution and the column allowed to drain. The fibre was then transferred to a Soxhlet extractor and extracted with carbon tetrachloride. Analysis of the recovered extract showed that 2.1 mg of β-carotene had been obtained from the Dunaliella cells which had been adsorbed on the polyester fibre.

EXAMPLE 4

The procedure of Example 3 was followed except that the polyester fibre was replaced by 1 g of nylon fibre. Analysis of the carbon tetrachloride extract showed that 0.5 mg of β-carotene had been recovered.

EXAMPLE 5

Polytetrafluoroethylene fibre (1.5 g) was activated by heating to 316° C. in 98% sulphuric acid and sufficient nitric acid was added to decolourize the mixture. The fibre was recovered, washed with water, dried and used in the procedure of Example 3. β-carotene (0.4 mg per gram of fibre) was recovered in the carbon tetrachloride extract.

EXAMPLE 6

Acrylic fibre (1 g) was treated as in Example 3 and 0.5 mg of β-carotene was recovered.

EXAMPLE 7

Anthracite (12.5 g) was ground to pass a 120-mesh (BSS) sieve and then stirred for 30 minutes with saturated sodium chloride solution (250 ml) containing $2 \times 10^5$ cells/ml of *Dunaliella salina*. The stirrer was then stopped and the mixture allowed to settle before the supernatant liquor was decanted and filtered through a plug of loosely packed glass wool. Both the sedimented material and that trapped on the filter were washed with saturated sodium chloride solution (20 ml) and the washings discarded. The filter plug was transferred to the same container as the sediment and the combined solids washed with successive portions of methylene dichloride until the washings were no longer coloured by β-carotene. The methylene dichloride solution was analysed and found to contain 0.7 mg of β-carotene per gram of anthracite used.

EXAMPLE 8

Graphite (12.5 g) was used in place of anthracite and the procedure of Example 7 repeated. The methylene dichloride solution was analysed and found to contain 0.6 mg of β-carotene per gram of graphite.

EXAMPLE 9

Chalcopyrite (12.5 g) was used in the procedure of Example 7 and 0.6 mg of β-carotene was recovered per gram of chalcopyrite.

EXAMPLE 10

Sphalerite (12.5 g) was used in the procedure of Example 7 and 0.25 mg of β-carotene was recovered per gram of sphalerite.

EXAMPLE 11

Pyrolusite (12.5 g) was used in the procedure of Example 7 and 0.25 mg of β-carotene was recovered per gram of pyrolusite.

EXAMPLE 12

Rutile (12.5 g) was used in the procedure of Example 7 and 0.2 mg of β-carotene was recovered per gram of rutile.

EXAMPLE 13

Ilmenite (12.5 g) was used in the procedure of Example 7 and 0.4 mg of β-carotene was recovered per gram of ilmenite.

EXAMPLE 14

Magnetite (12.5 g) was used in the procedure of Example 7 except that a permanent magnet was used to separate the magnetite instead of a glass wool filter. The recovery of β-carotene was 3.3 mg per gram of magnetite.

EXAMPLE 15

50 g of haematite of approximately 120 mesh (BSS) particle size was dried at 105° C. for one hour then treated with 1.4 g of dichlorodimethylsilane in 280 ml of petroleum ether for 12 hours at 20° C. The petroleum ether was then removed on a suction filter and the treated haematite dried at 105° C. for one hour. 10 g of the dried treated haematite was added to one liter of a suspension of *Dunaliella salina* cells in saturated sodium chloride solution. The haematite was then recovered by decantation and magnetic attraction and extracted with 100 ml of dichloromethane. 81% of the β-carotene content of the *Dunaliella salina* used was recovered.

EXAMPLE 16

50 g of magnetite was treated with 2.5 ml of aminopropyltriethoxysilane and 2.5 ml of acetic acid in 250 ml of water for 10 minutes, then the liquid was partially removed by suction filtration to leave a moistened magnetite which was heated at 105° C. for 5 hours to complete the reaction of the silane with the magnetite. The treated magnetite was washed with 100 ml of ethanol and dried at 105° C. for one hour. A 10 g sample was taken and used as in example 15 to give an 84% recovery of β-carotene.

EXAMPLE 17

1 kg of magnetite of approximately 100 mesh (BSS) was treated with 2 l of a 1% solution of dichlorodimethyl silane in petroleum ether for 2 hours at room temperature. The petroleum ether solution was then removed by suction filtration and the treated magnetite dried at 105° C. for 1 hour. Two suspensions of *Dunaliella salina* in saturated sodium chloride solution were made containing respectively 0.5 mg/l and 5.0 mg/l of β-carotene. Portions of the dried magnetite were mixed into 3-litre aliquots of the *Dunaliella salina* suspensions for 5 minutes. The magnetite was then removed from the saline solutions using a magnet and extracted with 100 ml of hexane. The hexane solution was analysed colourimetrically for β-carotene by absorption of light of 460 nm wavelength.

The following recoveries of β-carotene were obtained using the concentrations of β-carotene in the suspensions and the quantities of magnetite indicated.

| βcarotene in suspension mg/l | Magnetite g | β-carotene recovery mg/g magnetite |
|---|---|---|
| 0.5 | 0.3 | 3.6 |
| 5.0 | 0.3 | 3.63 |
| 0.5 | 3.0 | 0.38 |
| 5.0 | 3.0 | 3.6 |

EXAMPLE 18

500 g of dried 120 mesh (BSS) magnetite was treated with 1 l of a 1% solution of dichlorodimethyl silane in petroleum ether at ambient temperature for 3 hours. The treated magnetite was separated from the solvent by decantation and draining, with the aid of a magnet, dried for ½ hour and then demagnetized. Any lumps still present were broken up. Seven 3 litre aliquots of brine containing *Dunaliella salina* (from a saltworks) were each mixed with 60 g of the silanized magnetite and stirred well for 5 minutes. The magnetite was then collected, using a magnet, and dried by suction filtration.

The seven lots of magnetite containing adsorbed *Dunaliella salina* thus obtained were combined and distributed evenly over the surface of fine glass wool which was then placed in one arm of U-shaped pressure vessel. The vessel was then inverted and 500 ml of liquid carbon dioxide (at 4000 kPa and 8° C.) introduced and allowed to repeatedly percolate through the glass wool by repeated inversion of the vessel. The liquid carbon dioxide was then drawn off and replaced by a fresh aliquot of the liquid. In all three 500 ml aliquots of liquid carbon dioxide were used. Evaporation of the carbon dioxide gave respectively 0.36, 0.38 and 0.15 g of a red oily liquid which on cooling to $-5°$ C. crystallized to give a total of 23 mg of β-carotene crystals.

We claim:

1. A method for harvesting algae of the genus Dunaliella from a suspension thereof in brine containing sodium chloride at a concentration of about 3M or above, characterized in that the algal suspension is contacted with an adsorbent having a hydrophobic surface so as to adsorb the algae thereon, and the adsorbent with the algae adsorbed thereon is separated from the brine, characterized in that the adsorbent is a finely divided material which has a high surface area and has a hydrophobic surface or has been treated to produce a hydrophobic surface.

2. A method as claimed in claim 1, characterized in that the separated adsorbent with the algae adsorbed thereon is washed with a cell-free brine containing sodium chloride at a concentration of about 3M or above so as to remove bacterial cells and other extraneous materials.

3. A method as claimed in claim 1 or claim 2, characterized in that the separated adsorbent is treated with water or a brine of lower salinity so as to release the adsorbed algae.

4. A process for the separation and recovery of the cell components of algae of the genus Dunaliella which have been harvested by the method of claim 1, characterized in that the separated adsorbent with the algae adsorbed thereon is contacted with a solvent which disrupts the cell membrane of the algae and releases the cell contents for recovery.

5. A process as claimed in claim 4, characterized in that the solvent selected extracts β-carotene from the disrupted cells leaving cell debris and insoluble cell components still adsorbed on the adsorbent.

6. A process as claimed in claim 5, characterised in that solvent-soluble components other than β-carotene are separated from the β-carotene and optionally recovered following the extraction.

7. A process as claimed in claim 4, characterized in that after extraction of the β-carotene, the adsorbent is washed with water or a dilute saline solution containing less than 1M sodium chloride to release the cell debris and other solvent-insoluble components from the adsorbent.

8. A process as claimed in claim 7, characterized in that glycerol and/or the cell debris is recovered from the wash liquor.

9. A process as claimed in claim 7, characterized in that the adsorbent is recycled for further use following removal of the adsorbed material.

10. A process as claimed in claims 4, characterized in that the solvent is a chlorinated hydrocarbon; an aromatic hydrocarbon, an aliphatic hydrocarbon or a mixture of any two or more of said solvents 11. A process as claimed in claims 4, characterized in that the solvent is liquid carbon dioxide.

12. A process as claimed in claim 1, characterized in that the adsorbent is an organic polymer.

13. A process as claimed in claim 1, characterized in that the adsorbent is a polymer selected from the class consisting of poly(alkylenes), polyesters, polyamides, polyacrylates, polyacrylonitriles and fluorinated polymers.

14. A process as claimed in claim 1, characterized in that the adsorbent is a mineral, or a natural or synthetic carbonaceous material.

15. A process as claimed in claim 1, characterized in that the adsorbent is selected from the class consisting of anthracite, graphite, chalcopyrite, sphalerite, pyrolusite, rutile, ilmenite, magnetite and haematite.

16. A process as claimed in claim 1, characterized in that the adsorbent is a material which has been rendered hydrophobic by treatment with a silane or silicone.

17. A process as claimed in claim 1, characterized in that the adsorbent is a silanized glass or mineral.

18. A process as claimed in claim 1, characterized in that the adsorbent is silanized magnetite or haematite.

19. A process for the separation and recovery of the cell components of algae of the genus Dunaliella which have been harvested by the method of claim 2, characterized in that the separated adsorbent with the algae adsorbed thereon is contacted with a solvent which disrupts the cell membrane of the algae and releases the cell contents for recovery.

* * * * *